United States Patent
Stiger

[11] Patent Number: 6,117,386
[45] Date of Patent: Sep. 12, 2000

[54] CENTERING PERFUSION DELIVERY CATHETER AND METHOD OF MANUFACTURE

[75] Inventor: Mark L. Stiger, El Cajon, Calif.

[73] Assignee: Medronic Inc., Minneapolis, Minn.

[21] Appl. No.: 09/070,338

[22] Filed: Apr. 30, 1998

[51] Int. Cl.[7] .................................................. B29C 49/00
[52] U.S. Cl. .......................... 264/526; 264/573; 425/522; 425/526
[58] Field of Search ..................... 264/523, 526, 264/536, 540, 573; 425/522, 526, 532; 604/96; 606/194

[56] References Cited

U.S. PATENT DOCUMENTS

| | | | |
|---|---|---|---|
| 3,194,041 | 7/1965 | Johnson | 264/573 |
| 3,205,287 | 9/1965 | Settembrini | 264/504 |
| 3,291,670 | 12/1966 | Usab | 264/540 |
| 5,295,995 | 3/1994 | Kleiman | 606/194 |
| 5,395,333 | 3/1995 | Brill | 604/101 |
| 5,540,659 | 7/1996 | Teirstein | 604/104 |
| 5,575,771 | 11/1996 | Walinsky | 604/96 |
| 5,643,171 | 7/1997 | Bradshaw et al. | 600/1 |
| 5,718,684 | 2/1998 | Gupta | 604/96 |
| 5,891,386 | 4/1999 | Deitermann et al. | 264/526 |

FOREIGN PATENT DOCUMENTS

| | | | |
|---|---|---|---|
| 47-35548 | 9/1972 | Japan | 264/536 |
| WO 95/26681 | 12/1995 | WIPO | |
| 98/11933 | 3/1998 | WIPO | |

*Primary Examiner*—Catherine Timm

[57] ABSTRACT

A method and apparatus for manufacturing a centering, perfusion catheter balloon. A mold member is formed having an axial aperture. A plurality of axially spaced sets of transverse holes through the mold member. Each set of holes includes one or more holes, with the holes in each succeeding set at a predetermined angle to the holes in the immediate preceding set. A tight fitting sleeve is provided around the mold member. A plastic tube is inserted into the axial hole and the assembly is heated and the tube is internally pressurized to cause the tube to expand the tube into the holes, forming outwardly extending knobs on the tube. The tube is cooled and fluid is evacuated from the tube, causing the tube to draw the knobs into the axial aperture to permit the completed tube to be withdrawn. The tube can then be assembled into a treatment catheter assembly with the knobs maintaining a treatment device centered in the balloon while the knobs allow fluid perfusion along the catheter.

18 Claims, 4 Drawing Sheets

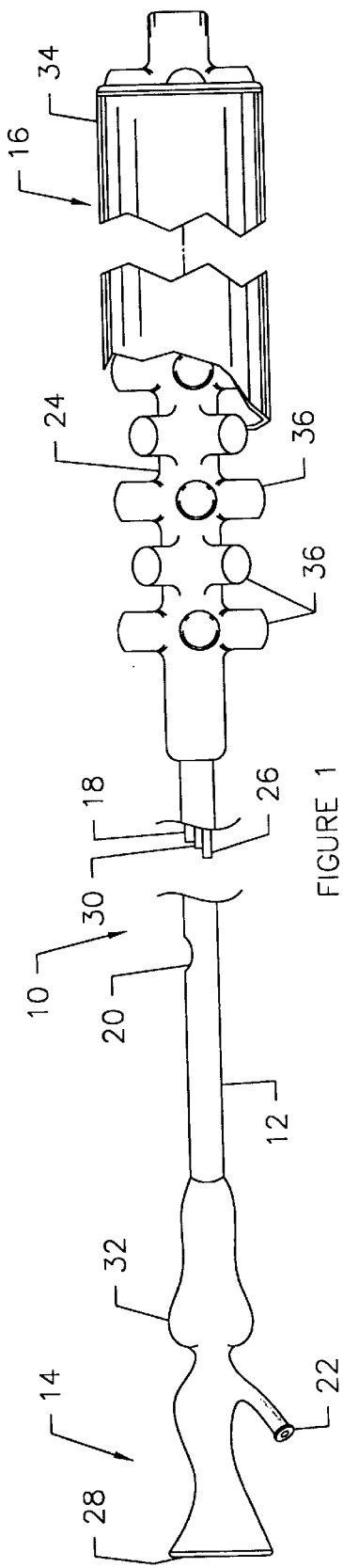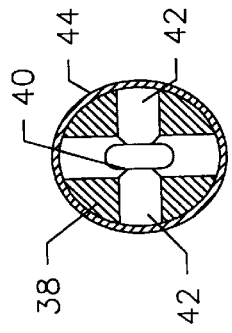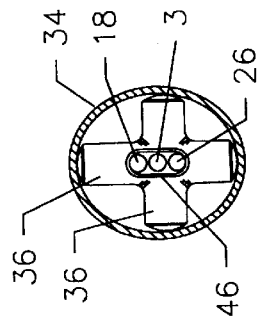

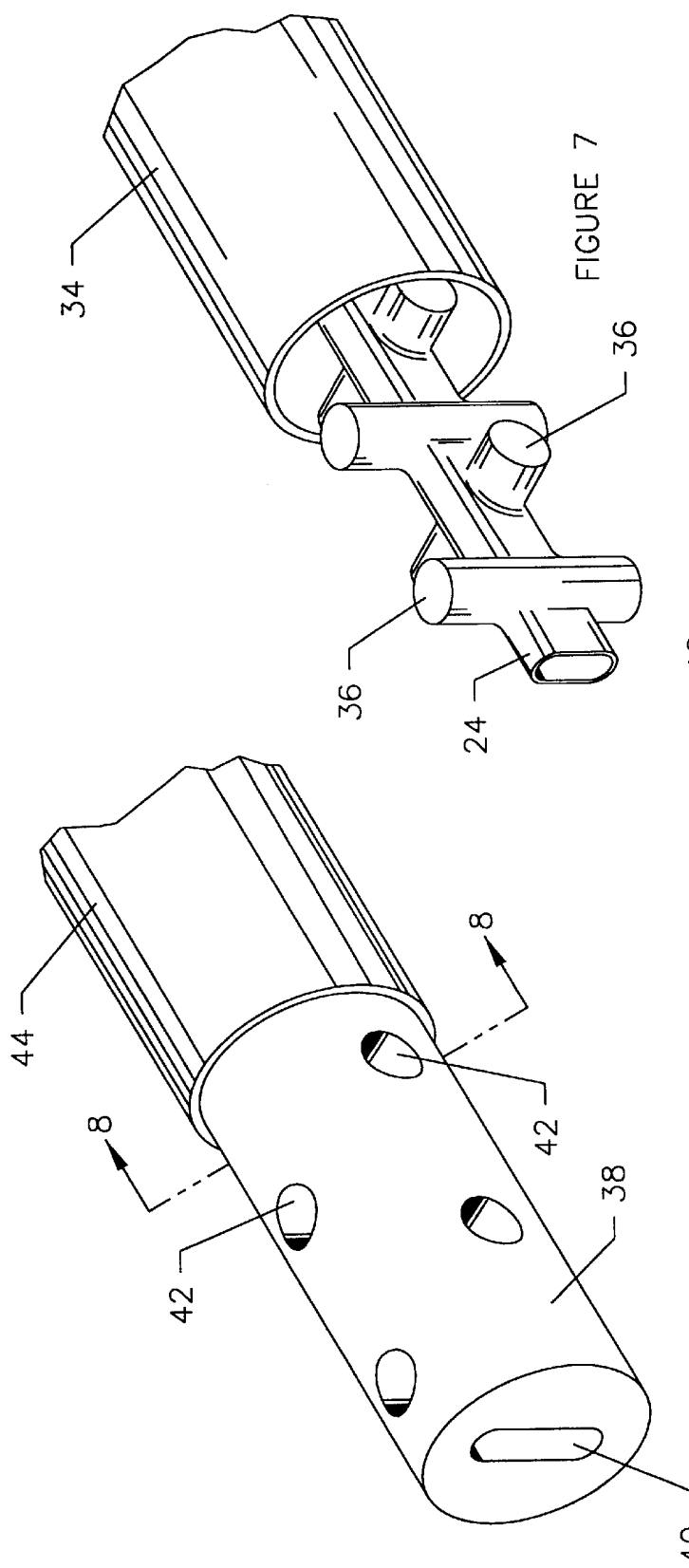
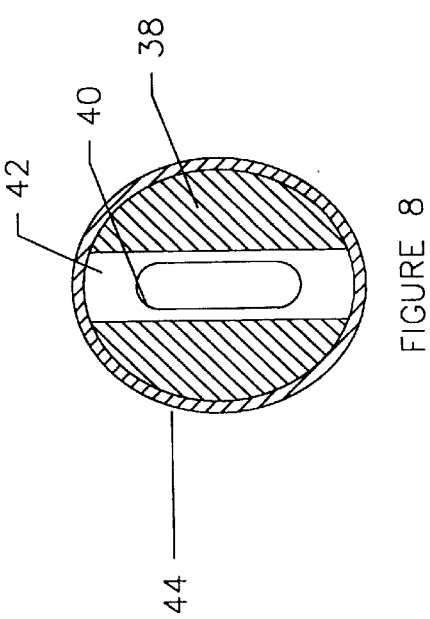

CENTERING PERFUSION DELIVERY CATHETER AND METHOD OF MANUFACTURE

FIELD OF THE INVENTION

This invention relates to an apparatus for supporting a therapeutic or investigative device in a body lumen, such as a coronary artery, which will center the device in the lumen for uniform treatment or for uniform investigative results. This also relates to the methods of manufacturing the apparatus and component that provides a means for centering the device in a body lumen. In to addition, the apparatus will allow fluid perfusion past the apparatus during the support of the therapeutic or investigative device.

BACKGROUND OF THE INVENTION

Percutaneous transluminal coronary angioplasty (PTCA) is often used to reduce arterial build-up of cholesterol fats or atherosclerotic plaque in coronary arteries. Typically a guidewire is inserted into an incision in an artery and is steered through the vascular system to the site of therapy. A guiding catheter, for example, can then be advanced over the guidewire and a balloon catheter advanced within the guiding catheter over the guidewire. The balloon at the distal end of the catheter is inflated causing the site of the stenosis to widen. While the stenosis or occlusion is greatly reduced, many patients experience a reoccurrence of the stenosis over a relatively short period. Researchers have found that angioplasty or placement of a stent in the area of the stenosis irritates the blood vessel causing rapid reproduction of the inner layer of blood vessel cells and restenosis through a mechanism called hyperplasia. It has been found that irradiating the blood vessel walls at the point of the stenosis will reduce or prevent hyperplasia. Precise control over the amount of radiation is important, since insufficient radiation will not prevent hyperplasia and excessive radiation can damage the blood vessel.

For treatment purposes utilizing radiation, a small radiation source is introduced into a body vessel such as a coronary artery and is maneuvered through the vessel to the site where restenosis is predicted to occur. Simply inserting a wire with a radioactive source secured in the wire at or near the distal end is effective in some cases. However, without full circumferential support the wire will tend to lie along one side of the vessel, so that the near side receives significantly more radiation than the opposite, distant, side. The near side could receive excessive, damaging, radiation exposure before the opposite side received the desired dose. Such a non-centering, wire-carried, radiation source is shown by Dake et al. in U.S. Pat. No. 5,199,939 and Bradshaw in U.S. Pat. No. 5,643,171. Therefore, it would be highly desirable to provide a radiation delivery system that would assure that the source is centered in the vessel.

Zoumboulis, in U.S. Pat. No. 3,324,847, describes a catheter having a spherical inflatable chamber adjacent the catheter distal end. A fluid containing a radioactive material such as radioactive iodine is pumped into the chamber, inflating the chamber and treating the vessel walls with ionizing radiation. The chamber will stop blood flow, so it can remain inflated for only a short period similarly to an angioplasty balloon as discussed below. Radiation source dwell times typically range from 3 to 30 minutes. Such extended blockage of the vessel will cause patient discomfort or pain and may eventually cause tissue damage. Further, precisely controlling radiation exposure while fully draining and refilling the chamber throughout the treatment can be very difficult.

A wire carrying a radioactive source could be inserted through a catheter lumen and advanced to the balloon located at the distal end of the catheter. The balloon would approximately center the source in the artery at the treatment site. As noted previously, irradiating a segment of an artery or the like generally requires some time, typically from about 3 to 30 minutes. Since a conventional angioplasty balloon substantially shuts off the blood flow through the artery, treatment can be conducted for only short periods before damage from lack of blood flow becomes significant.

Liprie, in international patent application publication number WO95/26681 describes a device for treating a vessel occlusion with radiation in which in a ribbed balloon catheter is inserted into a body vessel and inflated to provide perfusion between the ribs of the balloon. A wire carrying a radiation source is inserted into a lumen extending into the balloon area. This positions the radiation source generally near the center of the vessel. A lumen that is fairly well centered in the balloon when the balloon is in a straight vessel segment will tend to gravitate toward the inside of bend as the catheter is placed in a curved segment. This will result in uneven irradiation of the vessel wall on opposite sides. Further, the wide lobes shown by Liprie will not allow for adequate perfusion.

Other ribbed arrangements, using a double spiral rib or circumferential ribs are disclosed by Bradshaw et al. in U.S. Pat. No. 5,643,171 for centering a treatment lumen in a body vessel. These tend to be difficult to manufacture to the required tolerances. While useful, the lobes may not provide precise centering, especially if the treatment wire is not a good fit in the lumen. Similar to Liprie, supra, this configuration does not allow adequate perfusion.

Teirstein in U.S. Pat. No. 5,540,659 describes a series of centering wire loops or inflatable tubular coils for centering a wire-carried radiation source in a body vessel. Teirstein shows an embodiment in his FIGS. 5 and 6 an embodiment using flexible wires that can be expanded away from a central catheter. However, the use of a single set of wires extending from the distal to proximal ends of the treatment zone will tend to allow the catheter to tilt relative to the wires. Also, this system does not allow the use of multiple sets of expansion wires that could be opened independently to assure accurate placement. This complex arrangement of wires or inflatable coils is difficult to manufacture.

A series of approximately spherical balloons are used to center a radiation source in the arrangement of Verin et al. as disclosed in European patent application number 94109858.4. Although the source is centered in the vessel, lack of perfusion of blood past the site would permit only very short treatment times.

Thus, there is a continuing need for improved devices for delivering and centering a device in an endoluminal passageway or intravascular site within the body that can be easily and accurately inserted into and removed from even very small vessels and which accurately center the source in the vessel while permitting adequate perfusion so that treatment can be conducted over reasonably long periods. In addition, simple, practical and cost effective methods of manufacture of the centering component are required to effectively incorporate the use of the centering perfusion delivery catheter.

SUMMARY OF THE INVENTION

The above-noted problems, and others, are overcome in accordance with this invention by a catheter balloon and method and apparatus for manufacturing the catheter balloon which centers a device in a vessel while allowing perfusion past the balloon for the extended dwell times often required for a particular treatment.

The finished balloon component basically comprises an inflatable tube having a plurality of outwardly projecting protrusions. To manufacture such a balloon a mold member is prepared having a central axial opening with transverse holes providing radial openings at predetermined locations. A tube of suitable plastic material, such as polyethylene, is inserted into the mold axial opening and pressurized and the mold is heated to a suitable temperature. The tube expands into the sleeve and the transverse holes. Once the tube is permanently deformed into the balloon configuration, the mold is cooled and the pressure is removed. A slight negative pressure is imposed to collapse the balloon into the axial opening for removal from the mold. The balloon is then ready for securing to the balance of a catheter apparatus for use.

The combined centering and perfusion balloon comprises a plurality of knob-like protrusions extending outwardly from the narrow central tube. In the balloons made by the method of this invention, the protrusions comprise a plurality of spaced, approximately cylindrical, knobs. Any suitable number, size and spacing pattern may be used. The axial opening through the balloon will have a central treatment lumen for the treatment wire and will generally have an inflation lumen on one side of the treatment lumen and a guide wire lumen on the other side. In a body vessel, distal ends of the knobs contact the vessel wall, centering the catheter and allowing flow of blood between the knobs and thus past the catheter head.

In one preferred version of this configuration, a plurality of radial sets of two or more knobs are arranged along the catheter. The knobs in succeeding sets may be longitudinally aligned with knobs in the preceding set or may be sequentially staggered, as desired. In another preferred version of this configuration, knob sets are made up of pairs of knobs extending outwardly on opposite sides of the catheter. Succeeding pairs of knobs lie at a predetermined angle to the orientation of the preceding set. Optimally, each succeeding set is rotated about 45° to 90° to the orientation of the preceding set.

With each of the embodiments, a sheath may be provided over the protrusions, to prevent or reduce entrance of body vessel material into the perfusion channels between the knobs that would reduce perfusion effectiveness.

The overall apparatus, using the balloon made by the method of this invention, basically comprises an elongated tubular catheter assembly having a balloon at the distal end with at least one treatment lumen extending therethrough, and a set of interfacing connections, or a manifold, at its proximal end. The proximal end manifold, or manifolds, contain the connections that communicate with the lumens that extend through the catheter to is distal end. The Lumens that extend through the catheter are used for balloon inflation and deflation, guide wire passage and for the application of a treatment device. The treatment lumen is a closed end lumen that terminates at the distal end of the balloon and provides for the centering of the device that is placed within the lumen via the centering balloon produced by the method of this invention.

There are two possible configurations for the proximal interface of the treatment lumen. The first interface configuration consists of a connection that resides on the same component, or manifold, as the other catheter proximal interfaces, thus forming a single component for all catheter interfaces. The second configuration of the treatment lumen interface consists of a flexible extension lumen that is attached to, or passes through, the manifold containing the other catheter interfaces and is terminated with a separate component or manifold.

Once the centering balloon is secured to the catheter shaft, or assembly, it can take on two separate configurations. The first configuration allows for the balloon knobs, or protrusions, to be used as manufactured, or allows them to contact the vessel, or passageway, surface in which the balloon is centered. The second configuration consists of the addition of a thin sleeve, or sheath, that is placed over the balloon that provides a protective cylinder over the balloon when it is in its inflated condition. When the balloon is in its inflated state, the cylindrical sleeve acts as a barrier to foreign matter that may be present in the passageway that can occupy the interstitial spaces within the balloon protrusions, thus reducing the perfusion performance of the perfusion balloon.

Once the catheter assembly is guided through a vessel or passageway to the treatment site the balloon is inflated and the catheter treatment lumen of the catheter is centered along the central axis (straight or curved) of the body vessel. The balloon protrusions are spaced to permit blood or other medium to perfuse past the inflated balloon at an acceptable rate.

Any conventional insertion means, such as a conventional cardiac catheter, may be used for introducing the catheter into a body vessel or other passageway. Other practices or methods of insertion into the body may be used to provide entrance positioning in other intraluminal passageways in the body.

Current cardiac catheterization involves forming a small slit in either a femoral or brachial artery and introducing a guiding wire and guide catheter into the artery. The guide wire is positioned in the vasculature through the small slit. A guide catheter is placed over the guide wire and through the slit and serves as a delivery/introduction means for the centering delivery catheter, thus facilitating its positioning at the treatment site, or vascular stenosis. Current practices position the guide wire, guide catheter and other devices used internal to the body. Fluoroscopy highlights radiopaque segments in the device to aid in positioning. Prior to vascular treatment the guide wire is positioned so that it passes through the vascular stenosis, or treatment site, so that its tip rests appropriately distal to the treatment site.

The centering delivery catheter is slid over the guide wire that has been placed in the vessel and is positioned so that the centering balloon of the catheter is aligned with the treatment site. Hydraulic pressure is applied to the manifold connection that communicates with the internal surfaces of the centering balloon, thus inflating the balloon so that the protrusions contact the inside surface of the vessel at the treatment site. Once the balloon is fully inflated the treatment lumen of the centering delivery catheter is axially centered inside the treatment site. A radioactive tipped wire, or treatment device, is then inserted through the proximal interface that communicates with the treatment lumen and is slid through the closed treatment lumen until it encounters a lumen stop at the distal side of the centering balloon.

For treatments involving radiation, the radioactive treatment wire is allowed to dwell for a predetermined time period corresponding to the radiation dose desired for treatment. Once the dose has been delivered, the radiation delivery wire is removed. The hydraulic pressure is then relieved from the balloon and the balloon is evacuated, reducing the centering balloon protrusions back to a low profile near the catheter centerline. The centering delivery catheter can then be removed from the body by pulling it back over the guide wire and through the guide catheter. The guide wire and guide catheter are then removed and the procedure is complete.

BRIEF DESCRIPTION OF THE DRAWING

Details of the invention, and of preferred embodiments thereof, will be further understood upon reference to the drawing, wherein:

FIG. 1 is a side elevation of a catheter assembly including the centering/perfusion catheter balloon made by the method and apparatus of this invention;

FIG. 2 is a schematic perspective view of the mold apparatus for molding the knobby centering perfusion catheter balloon of this invention;

FIG. 3 is a schematic perspective view of the balloon produced by the mold apparatus of FIG. 2;

FIG. 4 is a section view taken on line 4—4 in FIG. 2;

FIG. 5 is a section view taken on line 5—5 in FIG. 3;

FIG. 6 is a schematic perspective view of a second embodiment of the mold apparatus;

FIG. 7 is a schematic perspective view of the balloon produced by the mold apparatus of FIG. 6;

FIG. 8 is a section view taken on line 8—8 in FIG. 6;

DETAILED DESCRIPTION OF PREFERRED EMBODIMENTS

Figure 10:
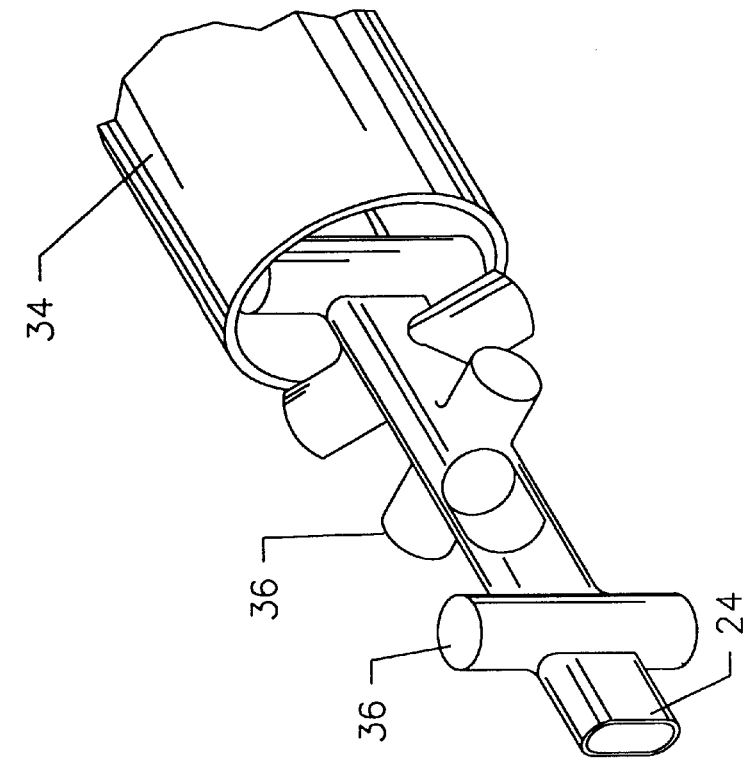
FIG. 10 is a schematic perspective view of the balloon produced by the mold apparatus of FIG. 9.

Referring to FIG. 1, there is seen a typical catheter assembly for use in the treatment of a predetermined section of a body vessel. This catheter assembly includes a catheter balloon, made by the method of this invention, for centering a treatment device within a catheter in a body vessel and for allowing fluid perfusion past the treatment site.

FIG. 1 shows an entire catheter assembly 10 for a rapid exchange catheter. Those skilled in the art would recognize that an over-the-wire assembly or another assembly could be used as well. The catheter shaft 12 is formed from a flexible plastic and includes a manifold 14 at the proximal end and a catheter head 16 at the distal end. Several longitudinal lumens extend through catheter shaft 12 from manifold 14 to head 16, as seen in FIGS. 2 and 3. Typically the lumens and associated entrance ports include a guide wire lumen 18 extending within catheter 12 and having an exit port 20, an inflation port 22 to furnish inflating media to the catheter balloon 24 via an inflation lumen 26 extending within catheter 12 and a treatment device port 28 for introducing a treatment wire (not shown) into a treatment lumen 30. A stress relief collar 32 may be provided adjacent to manifold 14. A sheath 34 may be placed over balloon 24 to prevent vessel wall material entering between balloon knobs 36 and restricting perfusion between those knobs.

FIGS. 2 and 4 schematically illustrate a molding apparatus for making a first embodiment of a centering, perfusion, catheter balloon 24. Mold member 38 is basically a cylinder formed from a suitable material, such as stainless steel, brass, aluminum, ceramic or high temperature resistant plastic. Best results are generally obtained with a stainless steel or brass mold because of the desirable thermal characteristics of these materials.

Mold member 38 has an axial aperture 40 therethrough, typically formed by drilling and milling, casting or molding. Preferably, electrical discharge machining is used to form the opening due to the tight tolerances required. Aperture 40 may have any suitable cross section, to provide a formed balloon passage that receives a guide lumen 18 and a treatment wire lumen 30, (as seen in FIG. 1). The generally rectangular lumen with semicircular ends is preferred as conveniently holding the two lumens grouped at the balloon center, or to accurately hold the treatment lumen at the formed balloon center.

A plurality of transverse holes 42 are formed along mold 38, each passing through the centerline of the mold and intersecting axial aperture 40. While cylindrical holes 42 are preferred for ease of manufacture and optimum perfusion and centering, any other suitable approximately cylindrical configurations may be used. For example, holes 42 could be frustoconical or an inverted frusto conical shape with the cone frustum toward the mold centerline. In addition, while a generally circular cross section for holes 42 is preferred, if desired the cross section could be varied. For example, if desired the cross sections could be oval or elliptical, with the long axis of the shape generally aligned with the mold centerline to provide minimum resistance to perfusion.

The holes may be formed in any suitable pattern that provides the desired combination of precise centering and maximum perfusion. In FIGS. 2 and 4, the pattern has a series of two crossed (preferably at about 90° to each other) holes at each mold axial location, with each pair of holes spaced apart and rotated about 45° to the preceding set.

A snug fitting sleeve 44 is placed over mold member 38 to close the outer ends of holes 42 during the molding operation. Sleeve 44 can be made removable or can be permanently placed around member 38. Of course, in place of sleeve 44 holes in a solid block or the like, sized to receive mold member 38, could be used if desired.

In use, tube 46 of suitable catheter balloon material is inserted into mold member 38 and sleeve 44 is placed around the mold member. While tube 46 may be preformed to the cross section of axial aperture 40 as shown, if desired a round tube may be used, deforming to the axial aperture shape as it is inserted. The assembly is heated to the forming temperature of the tube material and inflating fluid pressure is introduced into tube 46 in a conventional manner and so that the tube is inflated. The assembly is cooled, the fluid pressure is released, a slight vacuum is imposed in the tube to retract the knobs formed in holes 42 back into axial aperture 40 and the formed catheter balloon is removed. This method is described in greater detail below.

Mold member 38 and holes 40 and 42 may have any suitable dimensions. Typically, mold member may have a length of about 42 mm and a diameter of about 3 mm. In that case, holes 42 would optimally have diameters of about 1.25 mm and each set of holes 42 would be spaced apart about 2 mm. Axial hole 40 would be sized to receive the selected catheter and desired lumens.

FIGS. 3 and 5 illustrate the centering, perfusion, balloon catheter formed by the molding apparatus of FIG. 2. A plurality of sets of knobs 36 are formed corresponding to holes 42. The ends of each knob 36 is curved, matching the inside surface of sleeve 44. The portions of tube 46 between sets of knobs 36 has the rounded rectangular shape of axial aperture 40, so that various lumens may be inserted into balloon 24. In each case, the centered lumen will be treatment lumen 30. Other lumens may included a guide lumen 18 and an inflation lumen 26.

If desired a sheath 34 may be fitted over knobs 36 and bonded thereto. The rounded knob ends formed against sleeve 44 conform to the inner wall of a body vessel or to the inner surface of a sheath 34. Sheath 34 helps prevent vessel material from intruding between knobs 36 and reducing perfusion. However, in many cases sufficient perfusion is obtained with the catheter balloon 24 without sheath 48.

FIGS. 6–8 illustrate another embodiment of the centering perfusion catheter balloon. As before, a mold 38 has an axial opening configured to receive various lumens including a centered treatment lumen. Here each set in the series of spaced hole sets is a single transverse hole 42 intersecting axial aperture 40 as seen in FIG. 8. In this embodiment each succeeding hole 42 is oriented about 90° relative to the next preceding hole to provide an alternating series of single transverse knob pairs 36 as seen in FIG. 7. This arrangement provides greater perfusion flow volume past the balloon at the expense of slightly less precise centering. A sheath 34 is preferred over knobs 36, since the greater spacing between knobs would tend to allow greater entry of material from the body vessel wall to enter between knobs and reduce perfusion.

Figure 9:
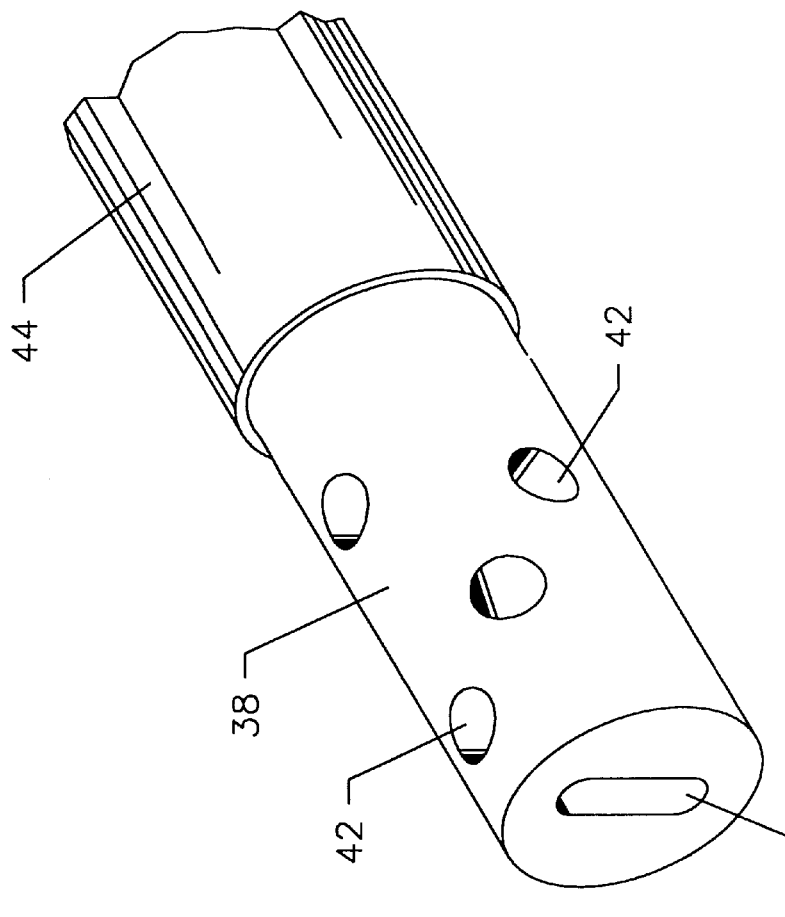
FIG. 9 is a schematic perspective view of a third embodiment of the mold apparatus.

A further embodiment of the centering perfusion catheter balloon of this invention is illustrated in FIGS. 9 and 10. Here mold 38 has an axial aperture 40 of the sort discussed above. Each set of holes 42 along the series of spaced holes is a single transverse hole. In this embodiment, each succeeding hole 42 is rotated about 45° relative to the next prior hole. This provides a generally spiral appearing pattern of knobs 36 along the catheter. Other rates of change in angle between succeeding knobs 36, such as 60°, could be used if desired. This is a preferred configuration, since the perfusion flow will be greater due to the lack of balloon protrusions that can impart resistance to flow. This knob arrangement provides much less overall flow restriction than would be the case with a continuous spiral rib since there will be greater flow area and additional flow paths than would be the case where liquid is passing along a continuous rib structure and forced to flow along a specific path. A sheath 34 over knobs 36 is preferred to reduce entry of material from a vessel wall into the space between the knobs and to provide additional support for centering.

Figure 11:
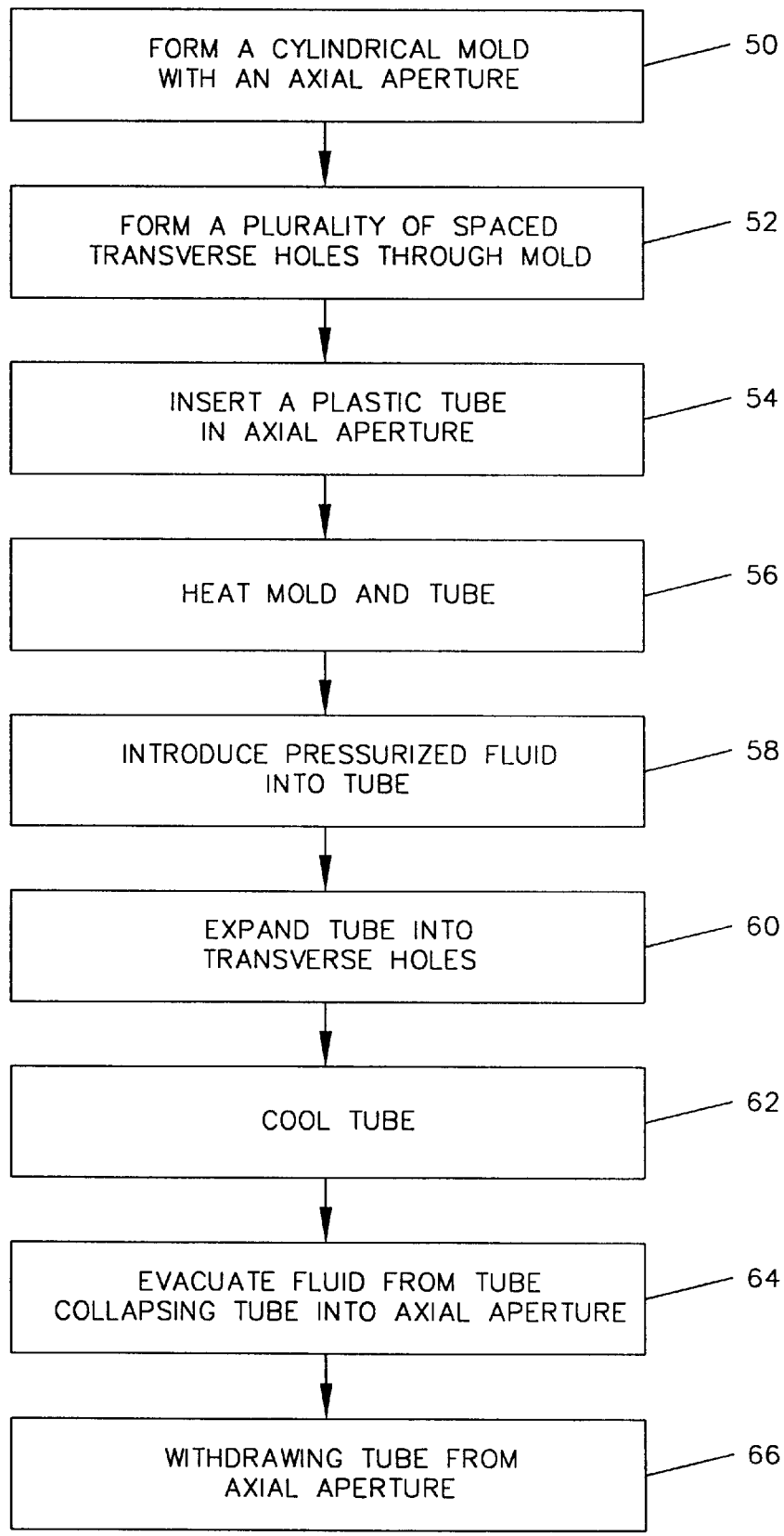
FIG. 11 is a block flow diagram illustrating the steps in the molding method.

FIG. 11 illustrates the mold apparatus and method of making a centering perfusion catheter having a series of sets of outwardly extending knobs.

Initially, a generally cylindrical mold member 38 having an axial opening 40 of predetermined cross section is formed by any suitable method, as indicated in FIG. 11, Block 50. Typically, the outer surface is machined and axial opening is formed by casting or electrical discharge machining. If desired, other methods may be used, such as molding from a plastic or powdered metal, etc. Any suitable material may be used for mold member 38. Typical materials include stainless steel, aluminum, high temperature resistant plastics and brass. Of these, stainless steel and brass are preferred because of their thermal characteristics and low cost.

A plurality of transverse holes 42 that intersect the axis of cylindrical mold 38 are then formed in the selected pattern, as indicated in Block 52. While holes may be formed by any suitable method, such as molding when the mold is formed, drilling, etc., electrical discharge machining is preferred for optimum convenience and precision in the small sizes being used. While circular holes 42 are preferred, the holes could have other cross sectional shapes, such as triangular, oval, elliptical, etc., if desired. Also, while cylindrical holes are preferred, if desired, the holes could be somewhat frusto conical with the conical base or apex at the distal knob end.

The mold assembly includes an outer sleeve 44 to close the ends of holes 42. A tubular sleeve is required to contain the balloon knobs 36 during forming to the desired shape. If desired, sleeve 44 could be formed from a material having a coefficient of thermal expansion less than that of mold 38, to tighten against the mold surface when heated. Of course, other outer mold members could be used, such as a hole in a metal block sized to receive mold 38, etc.

Next, as indicated in Block 54, a suitable plastic tube 46 is inserted into axial aperture 40. Any suitable material that has the desired expansion and catheter characteristics may be used. Typical tube materials include polyethylene and nylon. Of these, a polyethylene blend is preferred for optimum durability and softness. Tube 46 may have a cross section corresponding to that of axial aperture 40, may be round and pinched together for insertion or could be considerably smaller in cross section than the axial aperture, since the tube will expand to fill the aperture.

The assembly is then heated as indicated in Block 56 to the optimum expansion temperature for the plastic material selected, generally about the glass transition temperature of the plastic. Generally, the expansion temperature is about 260° F.

As indicated in Block 58, a fluid is introduced under suitable pressure into tube 46 to inflate the tube into the mold transverse openings 42, as indicated in Block 60. While any suitable fluid may be used, in general air is preferred. An inert gas, such as argon, may be used where air might oxidize the plastic material at the expansion temperature. Generally, the fluid inflation pressure ranges from about 200 to 450 psi. In some cases, pressurization of the tube may begin before full expansion temperature is reached.

Once expansion is complete, the mold assembly is cooled to a temperature at which the tube material is shape retaining, preferably to about room temperature, as indicated in Block 62.

Fluid is then evacuated from tube 46, as indicated in Block 64, until the tube is collapsed, with all of the now fully formed knobs 36 withdrawn into axial aperture 40. The completed knobbed centering perfusion catheter balloon is then withdrawn from axial aperture 40, as indicated in Block 66. Manufacture of the balloon in then complete and it is ready to be assembled into a complete centering, perfusion, catheter assembly of the sort illustrated in FIG. 1.

While certain specific relationships, materials and other parameters have been detailed in the above description of preferred embodiments, those can be varied, where suitable, with similar results. Other applications, variation and ramifications of the present invention will occur to those skilled in the art upon reading the present disclosure. Those are intended to be included within the scope of this invention as defined in the appended claims.

I claim:

1. A method of manufacturing a centering, perfusion, catheter balloon which comprises the steps of:

forming a generally cylindrical mold member having an axial aperture;

forming an axial series of sets of transverse holes through said mold member in a predetermined pattern of locations and relative angles;

inserting a plastic tube into said axial aperture, said plastic tube being expandable under heat and internal fluid pressure;

enclosing said mold member to cover said holes;

heating said mold member and plastic tube to a predetermined expansion temperature;

increasing pressure on a fluid in said plastic tube to a predetermined expansion pressure so that said plastic tube expands to fill said transverse holes forming projections corresponding to said holes;

cooling said plastic tube below said expansion temperature;

releasing said pressure in said plastic tube;

imposing a vacuum in said plastic tube to draw said projections into said axial aperture; and withdrawing said plastic tube from said axial aperture.

2. The method according to claim 1 wherein a single transverse hole forms each said set, and each succeeding set is oriented at a predetermined angle to the next preceding set.

3. The method according to claim 2 wherein each succeeding said set is oriented at an angle selected from the group consisting of about 45° and about 90° to the next preceding set.

4. The method according to claim 1 wherein each said set is formed from two transverse holes at about 90° to each other.

5. The method according to claim 4 wherein each succeeding said set is oriented at an angle of about 45° to the next preceding set.

6. The method according to claim 1 wherein said tube is formed from a plastic selected from the group consisting of pure polymers, copolymers, a polymeric mixture, or a polymeric blend.

7. The method according to claim 1 wherein said tube is formed from a plastic, said mold member is heated to a temperature of from about 230 to 260° F. and said tube is pressurized to a pressure of from about 200 to 450 psi.

8. The method according to claim 1 wherein said mold member is formed from a material selected from the group consisting of stainless steel, brass, copper, aluminum, high temperature resistant plastics and ceramics.

9. The method according to claim 1 wherein said axial aperture and transverse openings are formed by a method selected from casting and electrical discharge machining.

10. The method according to claim 1 wherein said axial aperture is formed with a cross section configuration of a rectangle with semicircular ends for receiving three lumens lying in the same plane.

11. An apparatus for forming a centering, perfusion, catheter balloon which comprises:

a generally cylindrical mold member having a central axis, an axial aperture through said mold member, a plurality of axially spaced sets of transverse holes through said mold member;

a sleeve for fitting over said mold member;

means for heating and cooling said mold member to a predetermined temperature; and means for pressurizing a tube placed in said axial aperture.

12. The mold apparatus according to claim 11 wherein each said set is a single transverse hole, and each succeeding set is oriented at a predetermined angle to the next preceding set.

13. The mold apparatus according to claim 12 wherein each succeeding said set is oriented at an angle selected from the group consisting of about 45° and about 90° to the next preceding set.

14. The mold apparatus according to claim 11 wherein each said set consists of two transverse holes at about 90° to each other.

15. The mold apparatus according to claim 14 wherein each succeeding said set is oriented at an angle of about 45° to the next preceding set.

16. The mold apparatus according to claim 11 wherein said mold member is formed from a material selected from the group consisting of stainless steel, brass, copper, aluminum, high temperature resistant plastics and ceramics.

17. The mold apparatus according to claim 16 wherein said sleeve is formed from a material having a lower coefficient of thermal expansion than said mold member material.

18. The mold apparatus according to claim 11 wherein said axial aperture has a cross section configuration of a rectangle with semicircular ends for receiving three lumens lying in the same plane.

* * * * *